US012802193B2

(12) United States Patent
Good et al.

(10) Patent No.: US 12,802,193 B2
(45) Date of Patent: Nov. 17, 2026

(54) SYSTEM AND METHOD FOR MEASURING AND REPORTING WINDROW MOISTURE

(71) Applicant: AGCO Corporation, Duluth, GA (US)

(72) Inventors: Grant Lewis Good, Moundridge, KS (US); Lucas Andrew Weller, Hesston, KS (US); Eric John Herbers, Hesston, KS (US)

(73) Assignee: AGCO Corporation, Duluth, GA (US)

( * ) Notice: Subject to any disclaimer, the term of this patent is extended or adjusted under 35 U.S.C. 154(b) by 215 days.

(21) Appl. No.: 18/719,913

(22) PCT Filed: Nov. 21, 2022

(86) PCT No.: PCT/IB2022/061199
§ 371 (c)(1),
(2) Date: Jun. 14, 2024

(87) PCT Pub. No.: WO2023/111724
PCT Pub. Date: Jun. 22, 2023

(65) Prior Publication Data

US 2025/0054121 A1 Feb. 13, 2025

Related U.S. Application Data

(60) Provisional application No. 63/265,539, filed on Dec. 16, 2021.

(51) Int. Cl.
*G06T 7/00* (2017.01)
*G01K 3/00* (2006.01)
(Continued)

(52) U.S. Cl.
CPC ............ *G06T 7/0002* (2013.01); *G01K 3/005* (2013.01); *G01N 33/0098* (2013.01); *G06T 7/60* (2013.01);
(Continued)

(58) Field of Classification Search
CPC ........... G06T 7/0002; G06T 7/60; G06T 7/90; G06T 2207/10024; G06T 2207/30188;
(Continued)

(56) References Cited

U.S. PATENT DOCUMENTS 10,717,099 B2 * 7/2020 Roberts .................. G01N 33/02
2007/0005208 A1 * 1/2007 Han ..................... A01B 69/001
701/50
(Continued)

OTHER PUBLICATIONS

Leone A, Romaniello R, Tamborrino A, Beneduce L, Gagliardi A, Giuliani M, Gatta G. Composting of Olive Mill Pomace, Agro-Industrial Sewage Sludge and Other Residues: Process Monitoring and Agronomic Use of the Resulting Composts. Foods. 2021; 10(9):2143. https://doi.org/10.3390/foods10092143 (Year: 2021).*
(Continued)

*Primary Examiner* — Atiba O Fitzpatrick

(57) ABSTRACT

A computer-implemented method of determining when a windrow of crop is ready to be baled. A sensor embedded in or passing over the windrow senses a characteristic of the windrow associated with a moisture content of the windrow and generates corresponding sensor data. A processing element analyzes the sensor data to determine whether the windrow is ready to be baled and provides an alert when the windrow is ready to be baled.

5 Claims, 3 Drawing Sheets

(51) Int. Cl.
*G01N 33/00* (2006.01)
*G06T 7/60* (2017.01)
*G06T 7/90* (2017.01)

(52) U.S. Cl.
CPC ...... *G06T 7/90* (2017.01); *G06T 2207/10024* (2013.01); *G06T 2207/30188* (2013.01)

(58) Field of Classification Search
CPC .. G01K 3/005; G01N 33/0098; G01N 33/245; A01F 15/08; A01F 15/00–2015/186; A01D 80/00; G06Q 50/02; G06V 20/188
See application file for complete search history.

(56) References Cited

U.S. PATENT DOCUMENTS

| | | | | |
|---|---|---|---|---|
| 2017/0013772 | A1* | 1/2017 | Kirk | A01F 15/071 |
| 2017/0086381 | A1* | 3/2017 | Roell | A01D 91/04 |
| 2018/0116121 | A1* | 5/2018 | Murray | A01D 78/00 |
| 2018/0116124 | A1 | 5/2018 | Murray et al. | |
| 2018/0317388 | A1* | 11/2018 | Gresch | A01D 41/1274 |
| 2020/0103904 | A1* | 4/2020 | Boydens | G05D 1/0212 |
| 2020/0208984 | A1* | 7/2020 | Boydens | G01C 21/20 |
| 2020/0264107 | A1* | 8/2020 | Bertolani | G01N 21/84 |
| 2021/0144802 | A1* | 5/2021 | Zafar | H04W 84/18 |
| 2022/0210975 | A1* | 7/2022 | Digman | A01F 15/00 |
| 2022/0381756 | A1* | 12/2022 | Baxter | H04Q 9/00 |

OTHER PUBLICATIONS

E. Reitbauer, C. Schmied and M. Wieser, "Autonomous Navigation Module for Tracked Compost Turners," 2020 European Navigation Conference (ENC), Dresden, Germany, 2020, pp. 1-10, doi: 10.23919/ENC48637.2020.9317465. (Year: 2020).*

Jin L et al: "Impact of pediococcus 1 pentosaceus and Pichia anomala in combination with chitinase on the preservation of high-moisture alfalfa hay", Grass and Forage Science, Blackwell Scientific Publications, Oxford, GB, vol. 73, No. 3, Feb. 15, 2018 (Feb. 15, 2018), pp. 610-621, XP071468706, ISSN: 0142-5242, DOI: 10.1111/GFS.12351 section 2.2.

European Patent Office, International Search Report related to International Patent Application No. PCT/IB2022/061199, mail date Jan. 25, 2023, 17 pages.

* cited by examiner

SYSTEM AND METHOD FOR MEASURING AND REPORTING WINDROW MOISTURE

CROSS-REFERENCE TO RELATED APPLICATIONS

This application is a national phase entry under 35 U.S.C. § 371 of International Patent Application PCT/IB2022/061199, filed Nov. 21, 2022, designating the United States of America and published in English as International Patent Publication WO 2023/111724A1 on Jun. 22, 2023, which claims the benefit of the filing date of U.S. Provisional Patent Application 63/265,539 "System and Method for Measuring and Reporting Windrow Moisture," filed Dec. 16, 2021, the entire disclosure of which is incorporated herein by reference.

BACKGROUND

Windrowers cut hay or other grain crops and deposit the cut crops into mounded rows called "windrows". After the windrows dry to a moisture content suitable for harvesting and storage, they are picked up and baled by round or square balers or other farm implements. In some operations two or more windrows are combined into a single larger row using, for example, a hay rake.

Determining when windrows are dry enough for baling is difficult because of variable weather conditions and variable initial crop moisture. Farmers therefore often spend a considerable amount of time driving to fields to visually inspect windrow conditions and often move baling equipment to fields prematurely, thus wasting time and resources.

Accordingly, there is a need for an improved system and method to determine when a windrow is ready to be baled or otherwise picked up and processed.

SUMMARY

The present invention solves the above-described problems and provides a distinct advance in the art of windrowers and balers. More particularly, the present invention provides a system and method for measuring and reporting windrow moisture content so as to better determine when the windrows are ready for baling or other processing.

An embodiment of the invention is a computer-implemented method of determining when a windrow of crop is ready to be baled. The computer-implemented method comprises: monitoring, via a sensor embedded in the windrow, a characteristic of the windrow associated with a moisture content of the windrow and generating corresponding sensor data; receiving, in a processing system, the sensor data generated by the sensor; determining, with the processing system, whether the windrow is ready to be baled based, at least in part, on the sensor data; and if the determining step determines the windrow is ready to be baled, providing an alert to an operator and/or control station that the windrow is ready to be baled.

In one embodiment, the sensor is a moisture sensor embedded in the windrow, and the characteristic of the windrow monitored by the moisture sensor is a moisture level in the windrow. The step of determining whether the windrow is ready to be baled comprises receiving, in the processing system, data representative of a target moisture level of the windrow; and comparing, with the processing system, the sensor data to the target moisture content to determine if the current moisture level of the windrow is at or below the target moisture content.

In other embodiments, the sensor may sense other characteristics of a windrow that are related to the windrow's moisture content. For example, the sensor may be a temperature sensor that monitors a current temperature of the windrow. Temperature is related to moisture content because higher windrow temperatures are generally associated with lower moisture content. In this embodiment, the step of determining whether the windrow is ready to be baled comprises receiving, in the processing system, data representative of a target temperature of the windrow; and comparing, with the processing system, the sensor data to the target temperature to determine if the current temperature of the windrow is at or above the target temperature.

In still other embodiments, the sensor may be a camera that monitors a size and/or color of the windrow to assess its moisture content. Windrow size is related to moisture content because a smaller and/or shrinking windrow size indicates a lower moisture content. Likewise, windrow color is related to moisture content because a darker windrow color may indicate a lower moisture content.

Once the processing system determines a windrow is ready to be baled, it generates and sends an alert. The alert may be a message sent to an operator station, mobile phone, etc. or instructions sent directly to a baler machine, tractor, or other machine or implement.

In some embodiments, the sensors may include GPS receivers or other location-determining components and may send location data to the processing system along with the sensor data. This allows the processing system to send the location of a dried windrow along with the alert.

Another embodiment of the invention is a method of creating a windrow of crop and determining when the windrow is ready to be baled. The method comprises: creating, with a windrow machine, the windrow; embedding at least one sensor in the windrow while the windrow is being formed; monitoring, via the sensor, a characteristic of the windrow associated with a moisture content of the windrow and generating corresponding sensor data; receiving, in a processing system, the sensor data generated by the sensor; determining, with the processing system, whether the windrow is ready to be baled based, at least in part, on the sensor data; and if the determining step determines the windrow is ready to be baled, providing an alert, via the processing system, that the windrow is ready to be baled.

This summary is provided to introduce a selection of concepts in a simplified form that are further described in the detailed description below. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

Figure 1:
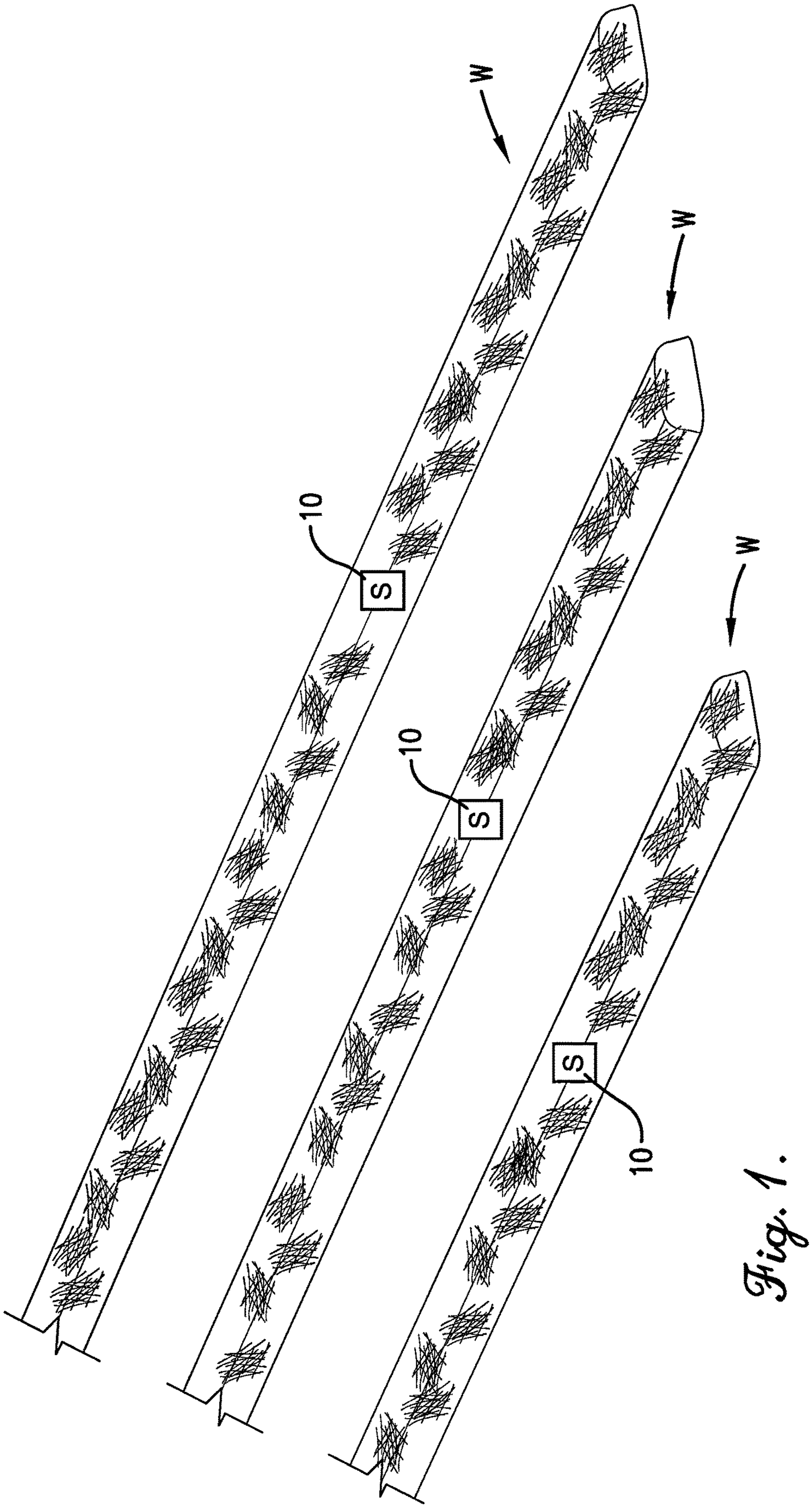
FIG. 1 is a schematic diagram of an agricultural field with a number of windrows created by a windrower with at least one sensor embedded in each windrow.

The drawing figures do not limit the present invention to the specific embodiments disclosed and described herein. The drawings are not necessarily to scale, emphasis instead being placed upon clearly illustrating the principles of the invention.

DETAILED DESCRIPTION

The present invention provides systems and methods for measuring and reporting windrow moisture content so as to better determine when windrows are ready for baling or other processing. In one embodiment depicted in FIG. 2, the systems and methods may be implemented with a plurality of sensors 10, a control system 12, and an operator station 14, but the invention is not limited to these particular components. FIG. 1 depicts a number of exemplary windrows W, with a sensor embedded in each windrow.

The sensors 10 may be any devices that can directly or indirectly sense characteristics associated with moisture content of a windrow and generate corresponding sensor data. In one embodiment, the sensors are moisture sensors that sense moisture levels in the windrows W and generate corresponding sensor data. The moisture sensors may be or include gypsum block sensors, neutron probes, gravimetric probes, time-domain reflectometry probes, frequency-domain reflectometry sensors, coaxial impedance dielectric reflectometry sensors, or any other sensor technologies that monitor moisture levels.

The sensors 109 may also sense windrow characteristics that are indirectly associated with moisture content. For example, in one embodiment, the sensors 10 may be temperature sensors that sense temperatures of the windrows. Temperatures are associated with moisture levels, as relatively higher temperatures may indicate relatively lower moisture contents.

In still other embodiments, the sensors 10 may be cameras that monitor a size or color of the windrows. The size of a windrow may be associated with moisture levels, as relatively smaller or shrinking sizes may indicate a relatively lower moisture content. Similarly, a windrow that starts to turn brown or other dark color versus green may indicate a relatively lower moisture content.

As shown in FIG. 1, at least one sensor 10 may be embedded in or otherwise placed within each windrow W. When used in this manner, the sensors 10 include wireless communication elements to transmit sensor data to the control system as described in more detail below. Some or all of the sensors may also include or be coupled with location-determining components such as GPS receivers to determine their locations and to transmit corresponding location data to the control system.

In other embodiments, one or more of the sensors 10 may be attached to a tractor or other machine and configured to monitor moisture content of the windrows as the machine passes over or by the windrows. In still other embodiments, some sensors 10 may be embedded in the windrows and others attached to a tractor or another moveable machine.

Although the drawing figures illustrate one sensor 10 in each windrow W, any number of sensors may be used without departing from the scope of the invention. For example, multiple sensors may be embedded in each windrow. Or, a single sensor may be embedded in just one windrow to monitor the moisture content of that windrow and to approximate the moisture content of the other windrows.

The control system 12 receives the sensor data from the sensors 10, determines when a windrow is ready to be baled or otherwise processed, and provides corresponding alerts or instructions to the operator station 14. The control system may be located in or adjacent the field in which the windrows are formed, in a nearby building or enclosure, or even in a remote location.

Figure 3:
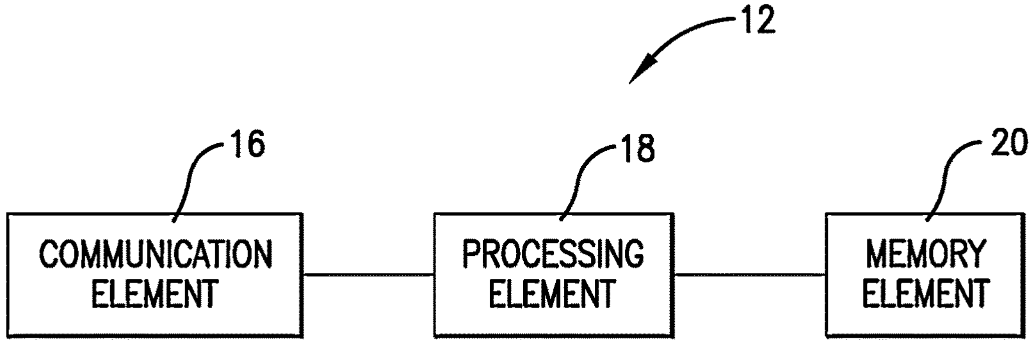
FIG. 3 is a block diagram of exemplary components of the control system.

As shown in FIG. 3, an embodiment of the control system 12 comprises a communication element 16, a processing element 108, and a memory element 20. The control system may also include other electronics, power sources, and components. The components of the control system need not be physically connected to one another since wireless communication among the components is possible and intended to fall within the scope of the present invention. Thus, portions of the control system may be located remotely from each other.

Some or all of the components of the control system 12 may be enclosed in or supported on a weatherproof housing for protection from moisture, vibration, and impact. The housing may be positioned anywhere and may be constructed from a suitable vibration and impact-resistant material such as, for example, plastic, nylon, aluminum, or any combination thereof and may include one or more appropriate gaskets or seals to make it substantially waterproof or resistant.

The communication element 16 receives the sensor data from the sensors 10 and sends alerts or instructions to the operator station 14. The communication element may include signal or data transmitting and receiving circuits, such as antennas, amplifiers, filters, mixers, oscillators, digital signal processors (DSPs), and the like. The communication element may receive and transmit data via RF signals and/or communication standards such as cellular 2G, 3G, 4G, 5G, or LTE, Wi-Fi, WiMAX, Bluetooth®, BLE, or combinations thereof.

The processing element 18 may include processors, microprocessors (single-core and multi-core), microcontrollers, DSPs, field-programmable gate arrays (FPGAs), analog and/or digital application-specific integrated circuits (ASICs), or the like, or combinations thereof. The processing element may generally execute, process, or run instructions, code, code segments, software, firmware, programs, applications, apps, processes, services, daemons, or the like. The processing element may also include hardware components such as finite-state machines, sequential and combinational logic, and other electronic circuits that can perform the functions necessary for the operation of the current invention. The processing element may be in communication with the other electronic components through serial or parallel links that include address busses, data busses, control lines, and the like.

The memory element 20 may include data storage components, such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element may be embedded in, or packaged in the same package as, the processing element. The memory element may include, or may constitute, a "computer-readable medium". The memory element may store the instructions, code, code segments, software, firmware, programs, applications, apps, services, daemons, or the like that are executed by the processing element.

The processing element 18 is programmed or otherwise configured to determine when a windrow is ready to be baled or processed based, at least partially, on the sensor data received from the sensors 10. In some embodiments, the processing element compares current windrow moisture levels, as reported by the sensors, to target moisture levels stored in the memory and determines a windrow is ready to be baled or processed when the current moisture level of the windrow is at or below the target moisture level. If the sensors are temperature sensors, the processing element compares current windrow temperatures, as reported by the sensors, to target temperature levels stored in the memory and determines a windrow is ready to be baled or processed when its current temperature is at or above the target temperature. If the sensors are cameras, the processing element compares current windrow sizes or color, as reported by the sensors, to historical or target sizes or colors stored in the memory and determines a windrow is ready to be baled or processed when its current size is less than a target size and/or when the windrow's current color is similar to a target color.

The operator station 14 receives the alerts and/or instructions from the control system 12. For example, the control system may send alerts or instructions to the operator station when a windrow is dry and ready to be baled or otherwise processed. In some embodiments, the operator station may be a computer, mobile phone, or hand-held computing device operated by a farmer or other operator. In other embodiments, the operator station may be a control system in a baler machine. In some embodiments, alerts are sent to multiple different devices.

Figure 4:
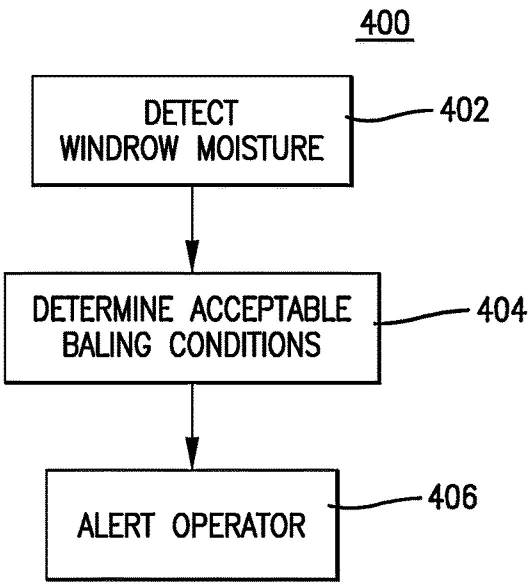
FIG. 4 is a flow diagram depicting exemplary steps of a method of the present invention.

The flow chart of FIG. 4 depicts the steps of an exemplary computer-implemented method 400 of determining when a windrow W of crop is ready to be baled. In some alternative implementations, the functions noted in the various blocks may occur out of the order depicted in FIG. 4. For example, two blocks shown in succession in FIG. 4 may in fact be executed substantially concurrently, or the blocks may sometimes be executed in the reverse order depending upon the functionality involved. In addition, some steps may be optional.

Figure 2:
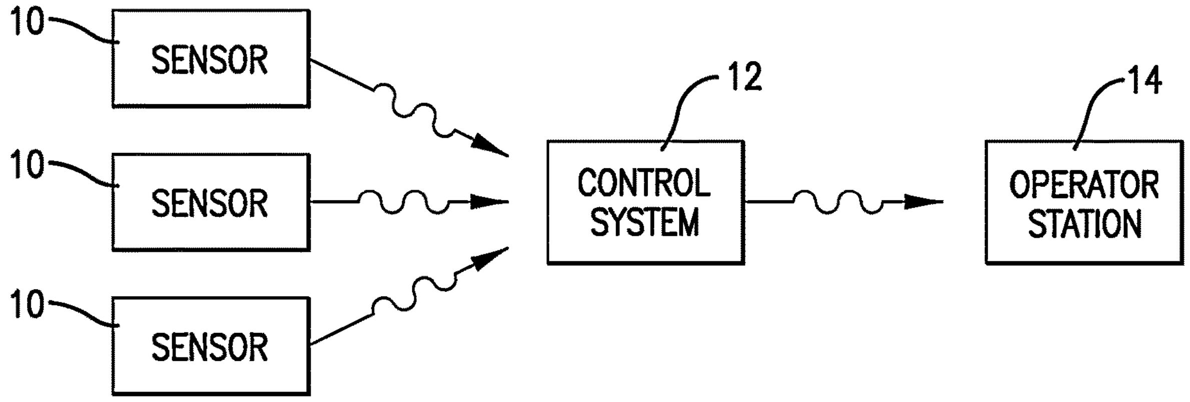
FIG. 2 is a block diagram of exemplary sensors, a control system, and an operator station that may be used to implement methods of the invention.

The method 400 is described as being executed by the devices and components introduced with the embodiments illustrated in FIGS. 1-3, but it may be executed by other devices and components. The steps of the method 400 may be performed by the control system or other devices through the utilization of the processing element and/or other processors, transceivers, hardware, software, firmware, or combinations thereof. However, some of such actions may be distributed differently among such devices or other devices without departing from the spirit of the present invention.

Some of the steps of the method may also be partially implemented with computer programs stored on one or more computer-readable medium(s) such as the memory. The computer-readable medium(s) may include one or more executable programs stored thereon, wherein the program(s) instruct one or more processing elements to perform all or certain of the steps outlined herein. The program(s) stored on the computer-readable medium(s) may instruct processing element(s) to perform additional, fewer, or alternative actions, including those discussed elsewhere herein.

As shown in step 402, one or more of the sensors 10 may monitor or detect a characteristic of a windrow associated with a moisture content of the windrow and generate corresponding sensor data. The sensor data is periodically or continuously transmitted to the control system 12. The sensors may also send location data and/or other data to the control system.

As shown in step 404, the processing element 18 then determines whether a windrow is ready to be baled based, at least in part, on the received sensor data. As described above, the processing element may compare current windrow moisture levels, as reported by the sensors 10, to target moisture levels stored in the memory and determine a windrow is ready to be baled or processed when the current moisture level of the windrow is at or below the target moisture level. In other embodiments, the processing element compares current windrow temperatures, as reported by the sensors, to target temperature levels stored in the memory and determines a windrow is ready to be baled or processed when its current temperature is at or above the target temperature. In still other embodiments, the processing element may compare current windrow sizes or colors, as reported by the sensors, to historical or target sizes or colors stored in the memory and determines a windrow is ready to be baled or processed when its current size is less than a target size and/or when the windrow's current color is similar to a target color.

As shown in step 406, the control system 12 generates and sends an alert to the operator station 14 if it determines a windrow is ready to be baled. If the operator station is a computer, mobile phone, or handheld computing device, the alert may be a message that indicates a windrow is ready to be baled. If the operator station is a control system of a baler or other machine, the alert may be a message or instructions to begin baling or processing a windrow. The alert and/or instructions may include the location of each windrow ready to be baled so that the operator or baler may navigate to the windrow(s).

Figure 5:
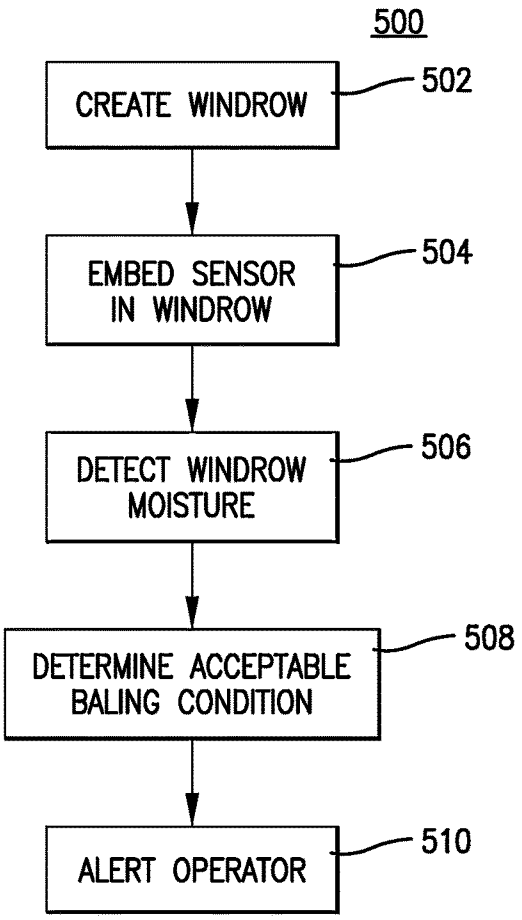
FIG. 5 is a flow diagram depicting exemplary steps of another method of the present invention.

The flow chart of FIG. 5 depicts the steps of an exemplary computer-implemented method 500 of creating a windrow of crop and determining when the windrow is ready to be baled. In some alternative implementations, the functions noted in the various blocks may occur out of the order depicted in FIG. 5. The method 500 is described as being executed by the devices and components introduced with the embodiments illustrated in FIGS. 1-3, but it may be performed with other devices. The steps of the method 500 may be performed by the control system through the utilization of the processing element and/or other processors, transceivers, hardware, software, firmware, or combinations thereof. However, some of such actions may be distributed differently among such devices or other devices without departing from the spirit of the present invention. Some of the steps of the method may also be partially implemented with computer programs stored on one or more computer-readable medium(s) such as the memory. The computer-readable medium(s) may include one or more executable programs stored thereon, wherein the program(s) instruct one or more processing elements to perform all or certain of the steps outlined herein. The program(s) stored on the computer-readable medium(s) may instruct processing element(s) to perform additional, fewer, or alternative actions, including those discussed elsewhere herein.

As shown in step 502, a windrower creates one or more windrows W of hay or other crop material. The windrower may be a Hesston by Massey Ferguson WR9900 Series windrower or any other conventional windrower.

In accordance with aspects of the present invention, the windrower is configured to embed sensors 10 in the windrows W while the windrows are created as shown in step

504. The windrower may include a bin for storing the sensors and a conveyor assembly or other feed mechanism for dropping the sensors in windrows along with cut crop.

As shown in step 506, once placed in a windrow, a sensor may monitor or detect a characteristic of the windrow associated with a moisture content of the windrow and generate corresponding sensor data. The sensor data is periodically or continuously transmitted to the control system. The sensors may also send location data and/or other data to the control system.

As shown in step 508, the processing element 18 then determines whether a windrow is ready to be baled based, at least in part, on the received sensor data. As described above, the processing element may compare current windrow moisture levels, as reported by the sensors, to target moisture levels stored in the memory and determine a windrow is ready to be baled or processed when the current moisture level of the windrow is at or below the target moisture level. In other embodiments, the processing element compares current windrow temperatures, as reported by the sensors, to target temperature levels stored in the memory and determines a windrow is ready to be baled or processed when its current temperature is at or above the target temperature. In still other embodiments, the processing element may compare current windrow sizes or colors, as reported by the sensors, to historical or target sizes or colors stored in the memory and determines a windrow is ready to be baled or processed when its current size is less than a target size and/or when the windrow's current color is similar to a target color.

As shown in step 510, the control system 12 provides an alert to the operator station 14 if it determines a windrow is ready to be baled. If the operator station is a computer, mobile phone, or handheld computing device, the alert may be a message that indicates a windrow is ready to be baled. The alert may also include the location of each windrow read to be baled. If the operator station is a control system of a baler or other machine, the alert may be a message or instructions to begin baling or processing a windrow. The instructions may include the location of each windrow read to be baled so that the baler may navigate to the windrow(s).

Additional Considerations

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the current technology can include a variety of combinations and/or integrations of the embodiments described herein.

Although the present application sets forth a detailed description of numerous different embodiments, the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as computer hardware that operates to perform certain operations as described herein.

In various embodiments, computer hardware, such as a processing element, may be implemented as special purpose or as general purpose. For example, the processing element may comprise dedicated circuitry or logic that is permanently configured, such as an application-specific integrated circuit (ASIC), or indefinitely configured, such as an FPGA, to perform certain operations. The processing element may also comprise programmable logic or circuitry (e.g., as encompassed within a general-purpose processor or other programmable processor) that is temporarily configured by software to perform certain operations. It will be appreciated that the decision to implement the processing element as special purpose, in dedicated and permanently configured circuitry, or as general purpose (e.g., configured by software) may be driven by cost and time considerations.

Accordingly, the term "processing element", "processing system", or equivalents should be understood to encompass a tangible entity, be that an entity that is physically constructed, permanently configured (e.g., hardwired), or temporarily configured (e.g., programmed) to operate in a certain manner or to perform certain operations described herein. Considering embodiments in which the processing element is temporarily configured (e.g., programmed), each of the processing elements need not be configured or instantiated at any one instance in time. For example, where the processing element comprises a general-purpose processor configured using software, the general-purpose processor may be configured as respective different processing elements at different times. Software may accordingly configure the processing element to constitute a hardware configuration at one instance of time and to constitute a different hardware configuration at a different instance of time.

Computer hardware components, such as communication elements, memory elements, processing elements, and the like, may provide information to, and receive information from, other computer hardware components. Accordingly, the described computer hardware components may be regarded as being communicatively coupled. Where multiple of such computer hardware components exist contemporaneously, communications may be achieved through signal transmission (e.g., over appropriate circuits and buses) that connect the computer hardware components. In embodiments in which multiple computer hardware components are configured or instantiated at different times, communications between such computer hardware components may be achieved, for example, through the storage and retrieval of information in memory structures to which the multiple computer hardware components have access. For example, one computer hardware component may perform an operation and store the output of that operation in a memory device to which it is communicatively coupled. A further computer hardware component may then, later, access the memory device to retrieve and process the stored output. Computer hardware components may also initiate communications with input or output devices, and may operate on a resource (e.g., a collection of information).

The various operations of example methods described herein may be performed, at least partially, by one or more processing elements that are temporarily configured (e.g., by software) or permanently configured to perform the relevant operations. Whether temporarily or permanently configured, such processing elements may constitute processing element-implemented modules that operate to perform one or more operations or functions. The modules referred to herein may, in some example embodiments, comprise processing element-implemented modules.

Similarly, the methods or routines described herein may be at least partially processing element-implemented. For example, at least some of the operations of a method may be performed by one or more processing elements or processing element-implemented hardware modules. The performance of certain of the operations may be distributed among the one or more processing elements, not only residing within a single machine, but deployed across a number of machines. In some example embodiments, the processing elements may be located in a single location (e.g., within a home environment, an office environment or as a server farm), while in other embodiments the processing elements may be distributed across a number of locations.

Unless specifically stated otherwise, discussions herein using words such as "processing," "computing," "calculating," "determining," "presenting," "displaying," or the like may refer to actions or processes of a machine (e.g., a computer with a processing element and other computer hardware components) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

The patent claims at the end of this patent application are not intended to be construed under 35 U.S.C. § 112(f) unless traditional means-plus-function language is expressly recited, such as "means for" or "step for" language being explicitly recited in the claim(s).

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A method of creating a windrow of crop and determining when the windrow is ready to be baled, the method comprising:

creating, with a windrow machine, the windrow;

embedding a sensor in the windrow while the windrow is created by the windrow machine;

monitoring, via the sensor, a characteristic of the windrow associated with a moisture content of the windrow and generating corresponding sensor data;

receiving, in a processing system, the sensor data generated by the sensor;

determining, with the processing system, whether the windrow is ready to be baled based, at least in part, on the sensor data;

if the determining step determines the windrow is ready to be baled, providing an alert, via the processing system, that the windrow is ready to be baled.

2. The method of claim 1, wherein the sensor is a moisture sensor and the characteristic of the windrow monitored by the moisture sensor is a moisture level in the windrow.

3. The method of claim 1, wherein the sensor is a temperature sensor and the characteristic of the windrow monitored by the temperature sensor is a temperature of the windrow.

4. The method of claim 2, wherein the step of determining whether the windrow is ready to be baled comprises— receiving, in the processing system, data representative of a target moisture level of the windrow; and comparing, with the processing system, the sensor data to the data representative of the target moisture content of the windrow to determine if the moisture level of the windrow is at or below the target moisture content.

5. The method of claim 3, wherein the step of determining whether the windrow is ready to be baled comprises— receiving, in the processing system, data representative of a target temperature of the windrow; and comparing, with the processing system, the sensor data to the data representative of the target temperature of the windrow to determine if the temperature of the windrow is at or above the target temperature.

* * * * *